United States Patent [19]

Schellhammer et al.

[11] Patent Number: 4,551,263
[45] Date of Patent: Nov. 5, 1985

[54] TRIAZOLIDINE-3,5-DIONES AS ACTIVATORS FOR PER-COMPOUNDS

[75] Inventors: Karl-Wolfgang Schellhammer, Berg.-Gladbach; Ludwig Rottmaier, Odenthal; Rudolf Merten; Ulrich Schimmel, both of Leverkusen, all of Fed. Rep. of Germany

[73] Assignee: Bayer Aktiengesellschaft, Leverkusen, Fed. Rep. of Germany

[21] Appl. No.: 417,722

[22] Filed: Sep. 13, 1982

[30] Foreign Application Priority Data

Sep. 16, 1981 [DE] Fed. Rep. of Germany ....... 3136808

[51] Int. Cl.$^4$ .......................... C11D 7/54; C11D 3/38; C11D 3/39
[52] U.S. Cl. ................................. 252/186.39; 252/98; 252/99; 252/102; 548/264
[58] Field of Search ............... 252/98, 99, 102, 186.39

[56] References Cited

U.S. PATENT DOCUMENTS

| | | | |
|---|---|---|---|
| 3,730,902 | 5/1973 | Disch et al. | 252/186.39 |
| 3,785,984 | 1/1974 | Berg et al. | 252/186.39 |
| 3,789,002 | 1/1974 | Weber et al. | 252/186.39 |
| 4,088,767 | 5/1978 | Shigematsu et al. | 548/264 |
| 4,329,245 | 5/1982 | Eymond et al. | 252/98 |
| 4,333,844 | 6/1982 | Duggleby et al. | 252/98 |
| 4,386,213 | 5/1983 | Giesecke et al. | 548/264 |

FOREIGN PATENT DOCUMENTS

| | | | |
|---|---|---|---|
| 0044417 | 1/1982 | European Pat. Off. | 548/264 |
| 2126538 | 12/1971 | Fed. Rep. of Germany . | |
| 3012922 | 10/1980 | Fed. Rep. of Germany . | |
| 2947619 | 5/1981 | Fed. Rep. of Germany . | |
| 1961076 | 6/1981 | Fed. Rep. of Germany . | |
| 893269 | 5/1962 | United Kingdom | 548/264 |

Primary Examiner—Alton D. Rollins
Attorney, Agent, or Firm—Sprung Horn Kramer & Woods

[57] ABSTRACT

Use of compounds of the formula

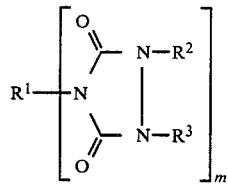

in which
$R^1$ designates hydrogen, an organic radical, the bonds $R^1$—N being C—N bonds, and, in the case in which m is 1, also acyl,
$R^2$ and $R^3$ designate hydrogen, an organic radical, the bonds $R^2$—N and $R^3$—N being C—N bonds, and acyl, and
m is an integer equal to the indicated valence of $R^1$, the compounds of the formula I furthermore containing at least one acyl group, as activators for per compounds, bleaching agents and detergents containing these activators, and new triazolidine-3,5-diones.

40 Claims, No Drawings

TRIAZOLIDINE-3,5-DIONES AS ACTIVATORS FOR PER-COMPOUNDS

The invention relates to the use of acylated triazolidine-3,5-diones as activators for per compounds, bleaching agents and detergents containing these activators, and to new triazolidine-3,5-diones.

It is known that inorganic per compounds, in particular perborates and percarbonates, are active substances in numerous bleaching agents, as used, for example, for bleaching and/or simultaneously washing textiles. However, the action of bleaching agents of this type is optimum only in the temperature range between 70° C. and 100° C. However, since the expenditure of energy is very high at this temperature, and since many textiles consist of synthetic fibres or of mixtures of synthetic and natural fibres and are thus very sensitive to relatively high wash temperatures, attempts are being made to reduce the wash temperature to 60° C. or lower, that is to say, to 30° C.

In the attempts to reduce the bleaching temperature and/or wash temperature, it has been found that per compounds become active even at relatively low temperatures, that is to say, below 60° C., when so-called activators, in particular cleavable N-acyl and O-acyl compounds, are added. Thus, for example, the use of tetraacetylethylenediamine is described in German Offenlegungsschrift No. 1,961,775, the use of inter alia tetraacetylmethylenediamine, trisacetyl cyanurate and acetylsalicylic acid is described in German Offenlegungsschrift No. 2,126,538, the use of acylated glycolurils is described in German Offenlegungsschrift No. 1,961,076, and the use of acylated 2,5-diketopiperazines is described in German Offenlegungsschrift No. 2,051,554.

A further group of activators which are readily obtainable and which have an activity superior to that of the activators known hitherto is now provided.

The present invention now relates to the use of compounds of the formula $$R^1 \left[ N \begin{array}{c} \diagup C(=O) - N - R^2 \\ \diagdown C(=O) - N - R^3 \end{array} \right]_m \quad \text{I}$$

in which
R$^1$ denotes hydrogen, an organic radical, the bond R$^1$—N being a C—N bond, or if m is 1, also acyl,
R$^2$ and R$^3$ designate hydrogen, an organic radical, the bonds R$^2$—N and R$^3$—N being C—N bonds, and acyl, and
m is an integer equal to the indicated valence of R$^1$, at least one of the radicals R$^1$, R$^2$ or R$^3$ representing an acyl group, as activators for per compounds.

The invention relates, in addition, to new triazolidine-3,5-diones of the formula I, in which R$^2$ and R$^3$ cannot simultaneously denote acetyl in the case in which m is 1.

The C atoms of the organic radical R$^1$, to which atoms the N atoms of the triazolidine-3,5-dione radicals are bonded, preferably belong to aliphatic, aromatic or mixed aliphatic/aromatic systems.

According to the invention the organic radical R$^1$ is substituted by 1 to 5, preferably 1 to 3 triazolidine-3,5-dione radicals.

They are preferably radicals of $C_1$–$C_{20}$-alkanes, $C_1$–$C_{12}$-alkanes, $C_1$–$C_6$-alkanes, $C_3$–$C_7$-cycloalkanes, benzene, naphthalene or phenyl-$C_1$–$C_6$-alkanes, it being possible for the hydrocarbons mentioned to be substituted, or they are radicals of hydrocarbons of the type $$X_1(C_nH_{2n}-X_2)_{\overline{n}}X_3$$

wherein
X$_1$, X$_2$ and X$_3$ designate optionally substituted cyclopentyl, optionally substituted cyclohexyl or optionally substituted phenyl, X$_1$, X$_2$ and X$_3$ preferably having the same meaning, and
n designates 1,2,3 or 4, or they are radicals of aliphatic ethers having 2–20 C atoms, aromatic ethers having 12–24 C atoms, mixed aliphatic/aromatic ethers having 7–24 C atoms, aliphatic tertiary amines having 3–20 C atoms, or aromatic tertiary amines having 8–24 C atoms.

The hydrocarbon radicals mentioned for R$^1$ can, for example, be substituted by ($C_1$–$C_4$-alkoxy)-carbonyl, CN or halogen, such as Cl, Br and F, and, in the case of aromatic radicals, also by lower alkyl, in particular $C_1$–$C_4$-alkyl.

The following preferred radicals R$^1$, represented by formulae, may be given as examples:

$$C_nH_{2n+1}- \quad n = 1 \text{ to } 8 \tag{a}$$

$$-(CH_2)_m- \quad m = 2 \text{ to } 12 \tag{b}$$

$$-\!\!\left[\begin{array}{c}CH_2-CH-O\\ \;\;\;\;\;\;\;\;\;\;\;|\\ \;\;\;\;\;\;\;\;\;\;R^8\end{array}\right]_p\!\!-CH_2-CH- \atop R^8 \tag{c}$$
$R^8 = H, CH_3$
$p = 1-9$ $$-\!\!\left[\begin{array}{c}CH_2-(CH_2)_q-N-\\ \;\;\;\;\;\;\;\;\;\;\;\;\;\;\;\;\;\;|\\ \;\;\;\;\;\;\;\;\;\;\;\;\;\;\;\;\;R^9\end{array}\right]_r\!\!(CH_2)_q-CH_2- \tag{d}$$
$R^9 = C_1-C_4-\text{alkyl}$
$q = 1-2$
$r = 1-4$ (e) phenyl, chlorophenyl (f) naphthyl (g) benzyl (phenyl-CH$_2$—)

-continued (h) 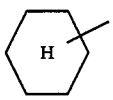

(i) 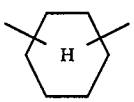

(j) 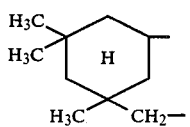

(k) 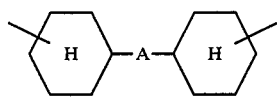

A = alkylene having 1-4 C atoms, O, —N(CH₃)—

(l) 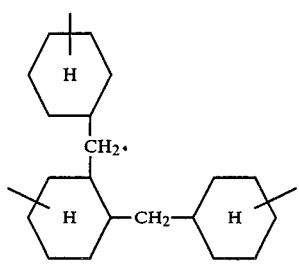

(m) 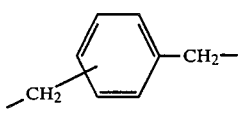

(n) 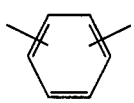

(o) 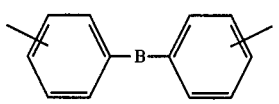

(p) 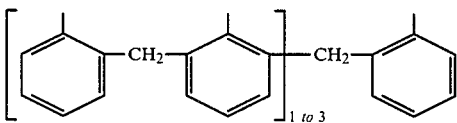

B = alkylene having 1-4 C atoms, O, —N(CH₃)—

(q) 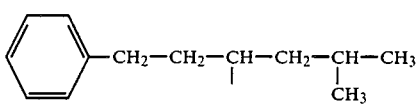

(r) C₄H₉—O—CH₂—CH₂—CH₂—
(s) —(CH₂)₃—O—(CH₂)$_{\overline{2\ to\ 4}}$O—(CH₂)₃—

(t)

$\underset{\text{CH}_3}{\underset{|}{\text{C}_6\text{H}_5}}$—CH₂—CH₂—CH—CH₂—CH—CH₃
                                      |
                                     CH₃

(u) H—

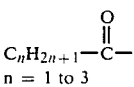
C$_n$H$_{2n+1}$—C(=O)—
n = 1 to 3

-continued (v) 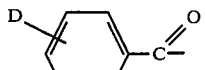

D = H, Cl, CH₃, NO₂.

R² and R³ preferably designate hydrogen, or C₁-C₁₀-alkyl which can be substituted, for example, by halogen, such as chlorine, bromine or fluorine, or by cyano, and particularly preferably designate aryl radicals as (C₁-C₈-alkyl)-carbonyl, benzoyl or phenyl-(C₁-C₄-alkyl)-carbonyl, it being possible for the acyl radicals mentioned to carry further substituents, such as, for example, C₁-C₄-alkoxy, halogen, such as Cl, Br or F, nitro or cyano.

Examples of R¹ and R² are: acetyl, propionyl, n-butyryl, i-butyryl, benzoyl, toluoyl, xyloyl, m-chlorobenzoyl, m-nitrobenzoyl and p-nitrobenzoyl.

In formula I, R² and R³ can be different; however, compounds having the same acyl radicals, in particular, are preferred.

Preferred compounds of the formula I are those with m=1 or 2 and R²=R³=acetyl, propionyl or benzoyl, and compounds with m=1 and R¹=R²=R³=acetyl, propionyl or benzoyl.

In formula I, m preferably represents 1, 2 or 3.

1,2,4-Triacetyl-triazolidine-3,5-dione, 1,2-bisacetyl-triazolidine-3,5-dione and 1,2-ethanediyl-4,4′-bis-[1,2-bis-acetyl-triazolidine-3,5-dione] are particularly preferred according to the invention.

Compounds of the formula I are prepared by acylating compounds of the formula II

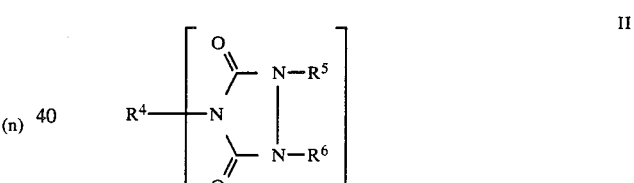

II in which
R⁴ designates hydrogen, an organic radical, the bonds R⁴—N being C—N bonds, and, in the case in which m' is 1, also acyl,
R⁵ and R⁶ designate hydrogen, an organic radical, the bonds R⁵—N and R⁶—N being C—N bonds, and acyl, and
m' designates an integer equal to the indicated valence of R⁴,
and at least one of the radicals R⁴, R⁵ or R⁶ represents hydrogen.

The compounds of the formula II can be prepared according to processes known from the literature.

1,2,4-Triazolidine-3,5-dione can be prepared from hydrazodicarbonamide, suspended in an organic, optionally water-miscible solvent, for example N-methylpyrrolidone, by cyclisation at temperatures from 150° C. to 280° C. and under a pressure of from 50 mbar to 5 bar, ammonia being split off, and the ammonia which has been split off being removed from the reaction mixture, and can be isolated after crystallisation (see German Offenlegungsschrift No. 2,947,619).

Starting compounds of the formula II, in which m' represents 1-5, R⁵ and R⁶ represent hydrogen and R⁴ represents a monovalent radical, or m=2 to 5, $R^5$ and $R^6$ represent hydrogen and $R^4$ represents a divalent to pentavalent radical, can be obtained from hydrazodicarbonamide and a primary monoamine or a polyamine having 2 to 5 primary amino groups, according to the process steps described above, ammonia being split off, and preferably 0.9 to 1.1 mols of hydrazodicarbonamide are employed per primary amino group.

These starting compounds of the general formula II can, as described, for example, in the chemical journal Zentralblatt 1898 I, 39, be converted into the activators according to the invention, of the general formula I, by acylation with the appropriate anhydride. of the formula

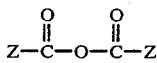

in which

Z designates $C_1$–$C_8$ alkyl, phenyl or phenyl($C_1$–$C_8$)-alkyl.

Thus, 1,2-bis-acetyltriazolidine-3,5-dione can be obtained by boiling 1,2,4-triazolidine-3,5-dione with acetic anhydride for ½ hour. The acylated triazolidine-3,5-diones of the general formula I which are not known from the literature can be prepared as well by acetation with the appropriate anhydride.

The activators, according to the invention, for per compounds, in particular inorganic per compounds, of the general formula I, are distinguished by a very good activating action and high solubility in water. The bleaching agents and/or bleaching detergents prepared using the acylated triazolidine-3,5-diones as activators show, in most cases, a substantially better activation than the activators known at present.

When choosing the amounts of activating agent to be added to the bleaching agents or detergents, it can be assumed in general that any acyl group which can be split off is capable of activating one active oxygen atom of the inorganic per compound used. For complete activation of the active oxygen of the inorganic per compounds which is employed, theoretically equivalent amounts of activating agent and organic per compound therefore have to be used. In practice, however, a substantially lower amount of activator is frequently sufficient. On the other hand, it is also possible to employ the activator in a large excess compared with the per compound. In general, the amount of activator to be employed is in the ratio of from 0.1 to 6, preferably from 0.2 to 1, of acyl radicals which can be split off per active oxygen atom of the per compound. In practice, the ratio used, of activator to inorganic per compound, is about 1:2 to 1:3 in most cases.

A particular advantage in using the compounds of the general formula I in bleaching agents and/or bleaching detergents containing per compounds is that activation of the per compounds and acceleration of the bleaching process and washing process already occur at relatively low temperatures, in particular at temperatures of from 40° to 60° C. This acceleration of the bleaching process and washing process may also still be observed at higher temperatures up to 100° C. This activation and acceleration of the bleaching process and washing process permits a decrease in the treatment temperature and/or reduction of the duration of washing, with an effect which remains constant, and this leads to substantial savings in time and/or energy in the washing process.

The conditions to be used in practice for the particular bleaching problem and washing problem, these conditions being temperature and duration of the treatment, concentration of the per compound and of the activator, and the pH value of the wash liquor, depend on the goods to be bleached or washed, or on the accompanying material present in the bleaching process. The concentration of the per compounds in most of the aqueous bleaching liquors or bleaching wash liquors is dependent, in particular, on the desired bleaching effect, and is adjusted in general such that the wash liquors contain about 10 to 500, preferably 50 to 300, mg of active oxygen/liter.

The bleaching process and/or washing process is normally carried out at a pH value of 6–12, preferably 8–11. However, since the action of the activators is associated with consumption of alkali, the known detergent compositions should contain sufficient amounts of strongly alkaline salts or appropriate buffer substances in order to prevent the pH value of the bleaching liquor or wash liquor from falling below the desired value. Examples of suitable alkaline salts or buffer substances which keep the pH value between 6 and 12 are phosphates, carbonates, bicarbonates or silicates of the alkali metals. The following may be mentioned as examples: sodium bicarbonate, sodium carbonate, potassium carbonate, sodium silicate, disodium hydrogen phosphate and sodium dihydrogen phosphate.

The activators according to the invention are preferably used in combination with inorganic per compounds, in bleaching agents and/or bleaching detergents for textiles. In addition to the goods of linen and cotton which must normally be treated at relatively high temperatures of 80°–100° C., particularly suitable textiles are also those goods which are produced from regenerated cellulose and other synthetic fibres, and from mixtures thereof, or which contain these fibres, and which are bleached or washed at low temperatures, preferably at 40° to 60° C. A particular advantage of the activators according to the invention for per compounds is that in bleaching or washing sufficient activation of the per compound is effected and a good bleaching effect is achieved, even at these low temperatures.

Inorganic per compounds which give $H_2O_2$ in aqueous solution are preferably used as per compounds. The perborates, persilicates, percarbonates and peroxyhydrates of the orthophosphates, pyrophosphates or polyphosphates of the alkali metals, in particular the sodium and potassium salts, are suitable in the main. Sodium perborate tetrahydrate is particularly preferably used as the per compound.

The activators according to the invention, in the form of powders or granules, can readily be mixed with the remaining constituents of the bleaching agent, detergent or washing auxiliary. In general, the particularly preferred bleaching detergents are obtained by mixing a washing powder, which is obtained by spray-drying and which as yet contains no per compound, with the pulverulent or granular activators and with the per compound. If the detergent according to the invention contains relatively large amounts of non-surfactant foam inhibitors and/or non-ionic surface-active agents present in liquid or pasty form, it is possible to spray these constituents onto the washing powder by the spray mist mixing process, and to mix the resulting product with the remaining constituents.

The bleaching detergents according to the invention may also be present in the form of two separate parts, one part containing the activator according to the invention, and the other part containing the detergent component, the per compound and, if appropriate, further additives. The activator can be packed in proportions suitable for use and such that it is protected from moisture, and can be used, for example, in the form of tablets or as packed portions to be used conjointly with activator-free bleaching detergents. When used in practice, the separately packed activator is added to the wash liquor shortly before or during the washing process.

To improve the storage stability of the activators according to the invention, these activators can be present in a form such that they do not come into direct contact with the remaining constituents of the bleaching agent or bleaching detergent, in particular with the per compounds concomitantly to be used according to the invention, and thus also cannot react prematurely. Although the acylated triazolidine-3,5-diones of the general formula I are distinguished by good stability to hydrolysis, it is advantageous to granulate these compounds, if appropriate, with a metal salt and/or with a complex former, and to protect them from moisture and from contact with the per compound by coating them. Suitable coating materials are organic substances which are water-soluble or water-insoluble, in particular which can be swollen in water, such as, for example, gelatine, methyl-, ethyl-, hydroxyethyl- and carboxymethylcellulose, and polyglycol ethers, long-chain fatty acids and alcohols, or polyvinyl alcohols.

This coating can be effected by known processes, as described in the case of known N-acyl compounds, for example, by coating with fatty acids (German Offenlegungsschrift NO. 2,221,492), with mixtures of fatty acids and polyglycols (German Offenlegungsschrift No. 2,207,974) and with mixtures of polyvinyl alcohol and carboxymethylcellulose (British Patent Specification No. 907,358).

The bleaching agents or bleaching detergents prepared using the activators according to the invention can furthermore have the compositions customary for these agents. In these agents, the mixture of activator and per compound can make up 10 to 100% by weight of the total composition. In textile detergents, the proportion of per compounds and activators is about 5 to 50, preferably 5 to 30, % by weight. The remaining components of such detergents are, in particular, surface-active agents in a proportion of about 5 to 40, preferably 10 to 30, % by weight, builders in a proportion of about 10 to 80, preferably 30 to 75, % by weight, and other detergent constituents and auxiliaries or additives, such as, for example, dirt-suspending agents, optical brighteners, dyestuffs, fragrances, enzymes, foam inhibitors, hydrotropic substances and water, in a proportion of about 0 to 15, preferably 1 to 10, % by weight.

The washing agents used are compounds which are known for this purpose and which can have anionic, cationic, zwitterionic or non-ionic character. These compounds contain at least one hydrophobic radical of, in most cases, 8-26, preferably 12-18, C atoms, and at least one anionic, cationic, zwitterionic or non-ionic water-solubilising group. The hydrophobic radical is in most cases a saturated aliphatic or alicyclic radical, preferably an aliphatic radical having preferably 12-18 C atoms.

It can be linked with the water-solubilising groups either directly or via intermediate members, for example via benzene rings, carboxylic acid ester groups or carbonamide groups, radicals, of polyhydric alcohols, which have ether-like or ester-like bonds, or polyether radicals.

Soaps composed of natural or synthetic fatty acids may be used as anionic surface-active agents. In addition, the sulphates and sulphonates are of practical importance among the synthetic anionic surface-active agents. These products include, for example, the alkylaryl sulphonates and aliphatic sulphonates, such as, for example alkanesulphonates, alkenesulphonates, hydroxyalkanesulphonates and hydroxyalkenesulphonates, and in addition fatty alcohol sulphates and sulphation products of oxalkylated alkylphenols, fatty acid amides or fatty acid alkylolamides having a content of about 1 to 20 ethoxy radicals and/or propoxy radicals in the molecule, and sulphated monoglycerides. The anionic washing actives suitable for use in detergents are described in detail, for example, in "Surface Active Agents and Detergents" by Schwartz, Perry and Berch, Vol. II (1958), pages 25 to 102.

Those products which owe the water-solubility of their hydrophobic molecular moiety to the presence of polyether chains, amine-oxide groups, sulphoxide groups or phosphine oxide groups, alkylolamide groupings or an accumulation of hydroxyl groups are used as non-ionic washing agents.

Of particular practical interest are the products which are obtainable by the addition of ethylene oxide and/or glycide to fatty alcohols, alkylphenols, fatty acids, fatty amines, fatty acid amides or sulphonic acid amides, and which can contain normally 6-40 and preferably 8-20 ether radicals, in particular ethylene glycol ether radicals, per molecule. Further details concerning the non-ionic surface-active agents are given, for example, in "Surface Active Agents and Detergents", Vol.II (1958), pages 120-143, the disclosure of which is hereby incorporated herein by reference.

The zwitterionic surface-active agents include those compounds which contain both acidic and basic hydrophilic groups, in addition to a hydrophobic alkyl radical having preferably 10-20 C atoms. The acidic groups include carboxyl, sulphonic acid, sulphuric acid half-ester, phosphonic acid and phosphoric acid partial ester groups. Suitable basic groups are primary, secondary, tertiary and quaternary ammonium groups. Such zwitterionic compounds having quaternary ammonium groups belong to the betaine type. Carboxy-sulphate and sulphonate betaines are of particular practical interest owing to their good compatibility with other surface-active agents.

Examples of such zwitterionic compounds are N-alkyl-beta-aminopropionic acid, N-alkyl-beta-iminodipropionic acid, N-alkyl-N,N-dimethyl glycine, or their salts, in particular sodium salts, and 1-alkyl-5-hydroxyethyl-5-carboxymethylimidazoline. The alkyl radicals are derived, for example, from stearyl alcohol, lauryl alcohol, coconut fatty alcohol, myristyl alcohol or cetyl alcohol, or from their industrial mixtures. Further examples of such zwitterionic surface-active agents are sulphobetaines which are obtained by the reaction of tertiary amines with sultones, and carboxybetaines which are obtained by the reaction of tertiary amines with chloroacetic acid or salts thereof, it being necessary for the tertiary amines to contain at least one hydrophobic alkyl radical.

The cationic surface-active agents include those compounds which owe the water-solubility of their hydrophobic molecular moiety to the presence of cationic water-solubilizing groups. Such cationic, solubilizing groups are amines and quaternary groups.

Of particular pratical interest among such compounds are N-alkylethylenediamine, it being possible for the alkyl radical to have 12 to 22 C atoms, such as, for example, N-2-amino-ethyl-stearylamine or N-myristylethylenediamine, and 2-aminoethyl-carboxylic acid amides, the carboxylic acid amides being derived from aliphatic $C_{10}$ to $C_{20}$ carboxylic acids, such as, for example, N-2-aminoethylstearylamide or N-2-aminoethylmyristylamide. Examples of typical quaternary ammonium compounds are ethyl-dimethyl-stearylammonium chloride, trimethyl-cetylammonium bromide, benzyl-dimethyl-stearylammonium chloride, benzyl-diethyl-stearylammonium chloride, trimethyl-stearylammonium chloride, dimethyl-ethyl-laurylammonium chloride and dimethyl-propyl-myristylammonium chloride, and the corresponding acetates and methosulphates.

The foaming power of the surface-active agents can be increased or reduced by combining suitable types of surface-active agents, just as it can be changed by the addition of non-surfactant organic substances.

The foaming power of the synthetic anionic or non-ionic surface-active agents can be reduced by the addition of soaps, in particular with those soaps which contain a high proportion of $C_{20}$–$C_{24}$ fatty acid constituents. The foaming power can be regulated by combinations of certain synthetic anionic surface-active agents, non-ionic surface-active agents and soaps. Furthermore, the addition compounds of propylene oxide to surface-active polyethylene glycol ethers are distinguished by a low foaming power.

A further essential group in the detergents is represented by the builders. Slightly acidic, neutral or alkaline inorganic or organic salts, in particular inorganic or organic complex formers, are suitable for this purpose. At least a part of these should have an alkaline reaction.

Examples of useful builders are the bicarbonates, carbonates, silicates or citrates of the alkali metals, and furthermore mono-, di- or tri-alkali metal orthophosphates, di- or tetra-alkali metal pyrophospates, and the metaphosphates known as complex formers. The water-soluble salts of higher-molecular polycarboxylic acids are also useful builders. Polymers of maleic acid, fumaric acid, itaconic acid, mesaconic acid, aconitic acid and methylenemalonic acid are particularly suitable polycarboxylic acids. Copolymers of these acids with one another or with other polymerizable substances, such as ethylene, propylene, acrylic acid, methacrylic acid, crotonic acid, vinyl acetate, acrylamide and styrene, are also suitable.

Suitable complex-forming builders are, in particular, the slightly acidic metaphosphates and the alkaline polyphosphates in particular tripolyphosphate. Examples of organic complex formers include nitrilotriacetic acid, ethylenediaminotetraacetic acid, N-hydroxyethylethylene-diamino-triacetic acid and similar compounds. Further suitable inorganic and organic builders are described in "Surface Active Agents and Detergents", Vol. II (1958), pages 289 to 317.

Products which have a stabilizing effect on the per compounds can be added, if appropriate, to the mixtures of the activators according to the invention and the per compounds. These compounds, which are known by the term stabilizers for per compounds, can be water-soluble or water-insoluble products, which can be added in amounts of up to 10% by weight, relative to the per compounds.

Particularly suitable water-insoluble per-compound stabilizers are alkaline earth metal silicates, in particular magnesium silicates, which are obtained in most cases by precipitation from aqueous solutions of alkali metal silicates using alkaline earth metal salts. Examples of further water-insoluble per-compound stabilizers are hydrated tin oxides.

Organic complex formers are particularly suitable water-soluble per-compound stabilizers which can be used completely or partially in place of the water-insoluble per-compound stabilisers.

In addition to the surface-active agents and the builders, still further auxiliaries and additives can be added to the mixtures of the activators according to the invention and to the per compounds.

These auxiliaries or additives can furthermore contain dirt-suspending agents which keep the dirt, which has been detached from the fibre, suspended in the wash liquor. Water-soluble colloids, of organic character in most cases, such as, for example, the salts of polymeric carboxylic acids, size, gelatine, salts of ether-carboxylic acids, carboxymethylcellulose, starch or polyvinylpyrrolidone, are suitable for this purpose.

The derivatives of diaminostilbenesulphonic acid, of diarylpyrazolines and of aminocoumarins may be particularly mentioned among the optical brighteners furthermore to be used.

Examples of brighteners from the group comprising the diaminostilbenesulphonic acid derivatives are compounds according to the formula III

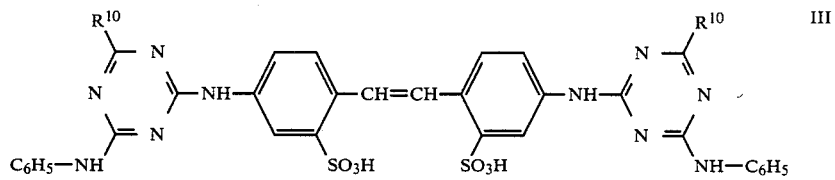

wherein
$R^{10}$ can denote the following radicals:
—$NH_2$, —$NH$—$CH_3$, —$NH$—$CH_2$—$CH_2$—$OH$, —$NH$—$CH_2$—$CH_2$—$OCH_3$, —$NH$—$CH_2$—$CH_2$—$CH_2$—$OCH_3$, $CH_3$—$N$—$CH_2$—$CH_2$—$OH$, —$N$=$(CH_2$—$CH_2$—$OH)_2$,

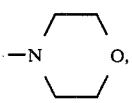

—$NH$—$C_6H_5$, —$NH$—$C_6H_4SO_3H$ and $OCH_3$.
The radical $R^{10}$ particularly denotes —$NH$—$CH_3$ or

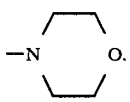

A further compound of the stilbene-sulphonic acid type is the following bis-triazolylstilbenesulphonic acid:

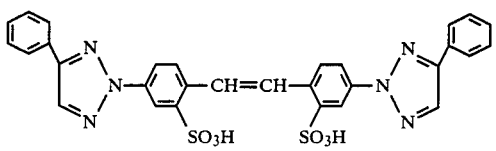

A further group of brighteners comprises the distyryl-biphenyl-disulphonic acids of the general formula IV

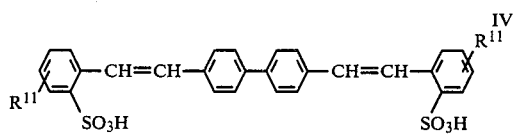

wherein $R^{11}$ preferably denotes hydrogen and/or chlorine.

A further group of optical brighteners comprises the diarylpyrazolines, of which those of the general formula V

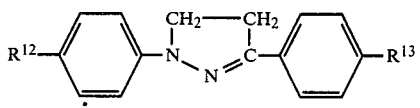

wherein, in the commercially available brighteners, $R^{13}$ can particularly represent Cl and $R^{12}$ can particularly represent Cl, $-SO_2-NH_2$, $-SO_2-CH=CH_2$ and $-COO-CH_2-CH_2-OCH_3$, are preferably used.

The brighteners furthermore include aliphatic or aromatic substituted aminocoumarins, for example 4-methyl-7-dimethylaminocoumarin or 4-methyl-7-diethylaminocoumarin.

Enzymes, in most cases mixtures of different enzymatic active compounds, for example proteases, lipases, ureases an amylases, can be used, in addition, as auxiliaries or additives for the bleaching agents or bleaching detergents according to the invention.

The bleaching agents or bleaching detergents according to the invention can furthermore contain dye-stuffs, fragrances, hydrotropic substances and water, in particular as water of crystallisation.

The preparation and the use of the activators according to the invention, of the general formula I, are illustrated by the examples which follow. In these examples, the percentage data denote percentages by weight, unless something different is expressly given.

EXAMPLES

Preparation of the acylated triazolidine-3,5-diones:

(1) 1,2-bisacetyl-triazolidine-3,5-dione

A mixture of 101 g of triazolidine-3,5-dione and 225 g of acetic anhydride is heated to 130° C., and is stirred for 30 minutes at 130° C. after the slightly exothermic reaction has ceased. After the mixture has cooled, it is filtered under suction, and the residue is washed with acetic acid and ethanol and dried at 60° C. under a pressure of 30 mbar.

150 g (=81% of theory) of 1,2-bisacetyl-triazolidine-3,5-dione of melting point 203°–205° C. are obtained.

$C_6H_7N_3O_4$ (185.1) Calculated: C=38.93%; H=3.81%; N=22.69%. Found: C=38.9%; H=3.7%; N=22.8%.

(2) 1,2,4-trisacetyl-triazolidine-3,5-dione

A mixture of 185 g of 1,2-bisacetyl-triazolidine-3,5-dione and 1 kg of acetic anhydride is stirred for 8 hours, while refluxing gently. Part of the solvent is distilled off. After the mixture has cooled, it is filtered under suction, and the residue is washed with acetic acid and then with ethyl acetate, and dried at 60° C. and under a pressure of 30 mbar. 152 g (=67% of theory) of 1,2,4-trisacetyltriazolidine-3,5-dione of melting point 137°–138° C. are obtained.

$C_8H_9N_3O_5$ (227.2) Calculated: C=42.29%; H=4.00%; N=18.50%. Found: C=42.2%; H=3.9%; N=18.6%.

(3) 1,2-ethane-diyl-4,4'-bis-[1,2-bisacetyl-triazolidine-3,5-dione]

A mixture of 456 g of 1,2-ethane-diyl-4,4'-bis-triazolidine-3,5-dione, 50 g of pyridine and 100 g of acetic anhydride is warmed to 130° C. and stirred for 1 hour at 130° C. After the mixture has cooled, the crystalline precipitate formed is filtered off under suction, washed with acetic acid and then with ethyl acetate, and dried at 60° C. and under a pressure of 30 mbar. 75 g (=95% of theory) of 1,2-ethane-diyl-4,4'-bis-[1,2-bisacetyl-triazolidine-3,5-dione] of melting point 226°–227° C. are obtained, and the structure of this compound is confirmed by IR and NMR spectra and elementary analysis.

$C_{14}H_{16}N_6O_8$ (396.3) Calculated: C=42.43%; H=4.07%; N=21.21%. Found: C=42.5%; H=4.1%; N=21.1%.

(4) 1,2-bispropionyl-1,2,4-triazolidine-3,5-dione

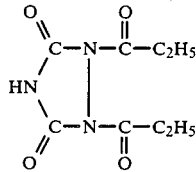

270 g of propionic acid anhydride are added dropwise to 101 g of 1,2,4-triazolidine-3,5-dione in 100 g pyridine at 100° C. within 2 hours. The reaction mixture is stirred for another hour at 100° C. to complete the reaction. After cooling the mixture to room temperature the precipitate is filtered off under suction, washed first with propionic acid and then with ethanol and is dried in vacuo at 70° C. 187 g (=88% of theory) of 1,2-bispropionyl-1,2,4-triazolidine-3,5-dione having a melting point of 208° C. are obtained.

$C_8H_{11}N_3O_4$ (213.2) Calculated: C=45.07%; H=5.20%; N=19.71%. Found: C=44.9%; H=5.1%.

(5) 1,2-bisacetyl-4-phenyl-triazolidine-3,5-dione

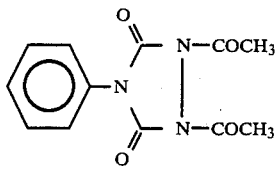

240 g of acetic anhydride are added dropwise to 177 g of 4-phenyl-triazolidine-3,5-dione in 100 g of pyridine at 100° C. within 30 minutes. To complete the reation the mixture is then stirred for 1 hour at 100° C. 500 ml of toluene are added to the hot solution, the mixture is cooled and the precipitate is filtered off under suction. 192 g of 1,2-bisacetyl-4-phenyl-triazolidine-3,5-dione having a melting point of 165° to 166° C. are obtained (from ethanol). After adding 150 ml of petroleum ether a further 37 g of the desired compound crystallized from the mother liquor. The assumed structure is confirmed by IR and NMR spectra as well as by elementary analysis.

$C_{12}H_{11}N_3O_4$ (261.2) Calculated: C=55.17%; H=4.25%; N=16.09%. Found: C=55.1%; H=4.1%; N=16.2%.

(6) 1,2-bis-(2-methyl-ethylcarbonyl)-4-phenyl-triazolidine-3,5-dione

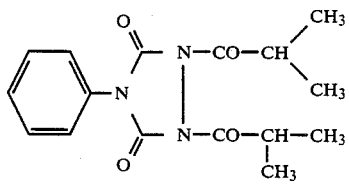

33 g of isobutyric acid anhydride are added dropwise to 17.7 g of 4-phenyl-triazolidine-3,5-dione and 20 g of pyridine at 100° C. The clear solution is stirred for 1 hour at 100° C. The solvent is then distilled off under a water pump vacuum and 40 ml of toluene are aded to the residue. 21 g of 1,2-bis-(2-methyl-ethyl-carbonyl)-4-phenyltriazolidine-3,5-dione having a melting point of 104° to 105° C. are obtained, the structure of which is confirmed by IR and NMR spectra and elementary analysis.

$C_{16}H_{19}N_3O_4$ (317.3) Calculated: C=60.56%; H=6.04%; N=13.24%. Found: C=60.7%; H=6.1%; N=13.4%.

(7) 1,2-bisacetyl-4-n-stearyl-triazolidine-3,5-dione

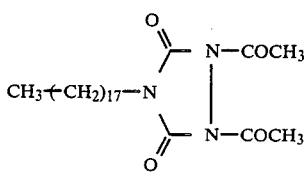

255 g of acetic anhydride are added dropwise to 353 g of 4-n-stearyl-triazolidine-3,5-dione and 1 kg of acetic acid at 120° C. The reaction mixture is stirred for 3 hours with refluxing to complete the reaction. After the mixture has cooled the crystalline precipitate is filtered off under suction, washed with acetic acid and ethyl acetate and dried. 290 g of 1,2-bisacetyl-4-n-stearyl-triazolidine-3,5-dione having a melting point of 100° to 101° C. (from ethyl acetate), the structure of which is confirmed by IR and NMR spectra and elementary analysis.

$C_{24}H_{43}N_3O_4$ (437.6) Calculated: C=65.87%; H=9.90%; N=9.60%. Found: C=66.1%; H=10.1%; N=9.8%.

(8) 4,4'-bis-[(1,2-bisacetyl)-triazolidine-3,5-dione-4-yl]-dicyclohexylmethane

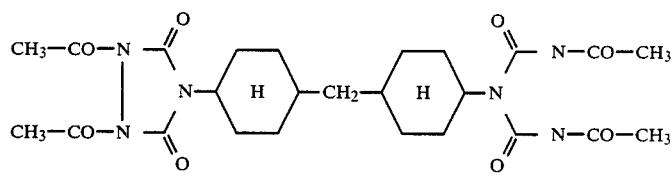

50 g of acetic anhydride are added dropwise to 37.8 g of 4,4'-bis-(triazolidine-3,5-dione-4-yl-dicyclohexylmethane and 50 g of acetic acid with refluxing within 30 minutes. The mixture is stirred for 2 hours with refluxing to complete the reaction. A part of the solvent is distilled off in vacuo from the clear solution and the residue is stirred with 100 ml of dioxane. After the mixture has cooled the precipitate is filtered off under suction, washed with dioxane and dried. 295 g of 4,4'-bis-[(1,2-bisacetyl)-triazolidine-3,5-dione] having a melting point of 252° to 253° C. are obtained, the structure of which is confirmed by IR and NMR spectra and elementary analysis.

$C_{25}H_{34}N_6O_8$ (546.6) Calculated: C=54.93%; H=6.27%; N=15.38%. Found: C=54.7%; H=6.1%; N=15.5%.

(9) 1,2-bisacetyl-4-methyl-triazolidine-3,5-dione

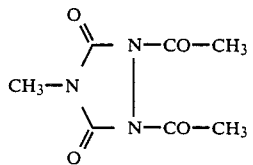

250 g of acetic anhydride are added dropwise to 115 g 4-methyl-triazolidine-3,5-dione and 150 g of acetic acid within 1 hour with refluxing. To complete the reaction the resulting clear solution is stirred for 3 hours with refluxing. Most of the solvent is distilled off in vacuo and the residue is recrystallized from 300 ml of dioxane, The precipitate is filtered off, washed with dioxane and dried. 108 g of 1,2-bisacetyl-4-methyl-triazolidine-3,5-dione having a melting point of 138° C. are obtained, the structure of which is confirmed by IR and NMR spectra and elementary analysis.

$C_7H_9N_3O_4$ (199.2) Calculated: C=42.20%; H=4.55%; N=21.10%. Found: C=42.0%; H=4.4%; N=21.1%.

(10) 1,2-bisacetyl-4-cyclohexyl-triazolidine-3,5-dione

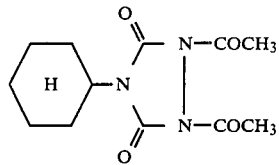

125 g of acetic anhydride are added dropwise to 91.5 g of 4-cyclohexyl-triazolidine-3,5-dione and 100 g of acetic acid within one hour at 110° C. The clear solution is stirred for 3 hours with refluxing. A part of the solvent is distilled off with refluxing and the residue is stirred with cyclohexane. After the mixture has cooled it is filtered under suction, washed with cyclohexane and dried. 78.5 g of 1,2-bisacetyl-4-cyclohexyl-triazolidine-3,5-dione having a melting point of 126° to 127° C. are obtained, the structure of which is confirmed by IR and NMR spectra and elementary analysis.

$C_{12}H_{17}N_3O_4$ (267.3) Calculated: C=53.92%; H=6.41%; N=15.70%. Found: C=54.1%; H=6.5%; N=15.6%.

USE EXAMPLES 11 TO 17

(a) A low-foam washing powder of the following composition was prepared by spray-drying:
- 12.0% of anionic surface-active agent (=Na alkyl-benzenesulphonate)
- 4.7% of non-ionic surface-active agent (fatty alcohol polyglycol ether having 11 mols of ethylene oxide)
- 4.0% of soap as a foam regulator
- 6.7% of sodium silicate ($Na_2SiO_3$)
- 2.0% of carboxymethylcellulose
- 19.0% of sodium sulphate
- 40.0% of sodium tripolyphosphate
- 0.3% of optical brightener
approx. 11.3% of residual moisture (b) Detergents, the compositions of which can be seen in Table 1 below, were prepared by subsequent admixture of the remaining constituents:

TABLE 1

| Example | 11 % | 12 % | 13 % | 14 % | 15 % | 16 % | 17 % |
|---|---|---|---|---|---|---|---|
| Regulated low-foam washing powder | 74.7 | 74.7 | 74.7 | 77.0 | 74.7 | 75.9 | 74.7 |
| Sodium perborate tetrahydrate | 22.0 | 15.0 | 15.0 | 15.0 | 15.0 | 15.0 | 15.0 |
| Magnesium silicate | 3.0 | 3.0 | 3.0 | 3.0 | 3.0 | 3.0 | 3.0 |
| Na ethylenediaminetetra-acetate | 0.3 | 0.3 | 0.3 | 0.3 | 0.3 | 0.3 | 0.3 |
| Tetraacetylethylenediamine | — | 7.0 | — | — | — | — | — |
| Triazolidine accord. to Example 2 compound B | — | — | 7.0 | 4.7 | — | — | — |
| Triazolidine accord. to Example 1 compound A | — | — | — | — | 7.0 | 5.8 | — |
| Triazolidine accord. to Example 3 compound C | — | — | — | — | — | — | 7.0 |

(c) Bleach-test fabrics immedial green WFK 10E were washed with these detergents from Table 1 at a detergent concentration of 5 g/liter and a liquor ratio of 1:20 in water of 18° German hardness for 30 minutes at 40° C. and for 30 minutes at 60° C., respectively. The washing process was carried out in a Launder-o-meter.

The brightenings achieved in these washing experiments were determined by reflectance measurements using a UV cut-off filter at 460 nm on the RFC 3 from Zeiss, according to DIN (German Industrial Standard) 44,983, sheet 1, page 3, as described by the Federal Materials Testing Institute/Berlin. The results of these investigations are summarised in Table 2.

TABLE 2

| | R values at 40° C., washed 4 times | at 60° C., washed 4 times |
|---|---|---|
| 11 | 33.2 | 36.7 |
| 12 | 37.8 | 42.3 |
| 13 | 38.7 | 46.8 |
| 14 | 37.4 | 42.7 |
| 15 | 38.0 | 45.2 |
| 16 | 36.6 | 44.0 |
| 17 | 37.6 | 43.5 |

The above results show that the detergent formulations with the activators according to the invention achieve a substantially better brightening compared to the detergent formulation without an activator, and that the detergent formulations with the activators according to the invention achieve a better brightening than the detergent formulation with the known and generally used activator tetraacetylenediamine, at the same concentration.

What is claimed is:

1. A composition comprising a per-compound and an activator, said activator being a compound of the formula

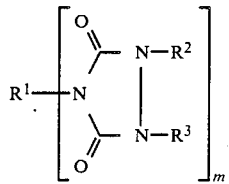

in which
R$^1$ is hydrogen, C$_1$–C$_{20}$-alkyl, C$_3$–C$_7$-cycloalkyl, phenyl, phenyl C$_1$–C$_7$-alkyl, C$_{1-4}$-alkylphenyl, halophenyl, the hydrocarbon moieties of which can be substituted by (C$_1$–C$_4$ alkoxy)-carbonyl, CN, or halogen, or
R$^1$ is as defined below for R$^2$ or is C$_4$H$_9$—O—CH$_2$CH$_2$CH$_2$— or a radical of the formulae —(CH$_2$)$_m$— with m = 2–12,

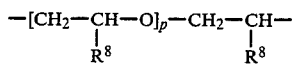

with R$^8$ = H or CH$_3$, and p = 1–9,
—(CH$_2$)$_3$—O—(CH$_2$)$_{2-4}$—O—(CH$_2$)$_3$—,

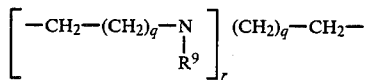

with R$^9$ = C$_{1-4}$ alkyl, q = 1–2, r = 1–4,

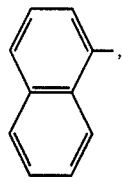

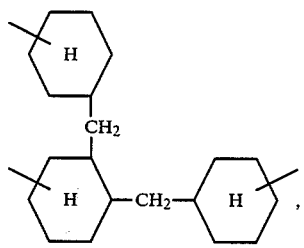

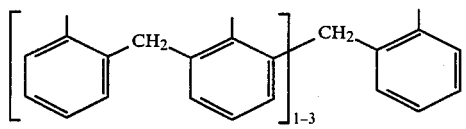

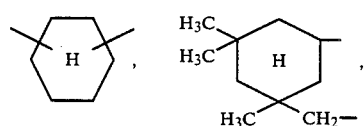

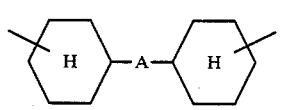

wherein A = Alkylene having 1–4 carbon atoms, —O— or —N—
                                                         |
                                                        CH$_3$

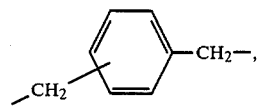

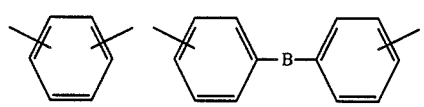

wherein B = alkylene having 1–4 carbon atoms, —O— or —N—
                                                         |
                                                        CH$_3$ R$^2$ and R$^3$ are unsubstituted or substituted C$_1$–C$_8$ alkyl carbonyl, benzoyl or phenyl C$_1$–C$_4$-alkylcarbonyl wherein the substituents are lower alkyl, C$_1$–C$_4$ alkoxy, halogen, nitro or cyano; and m is an integer equal to the indicated valence of R$^1$.

2. A composition according to claim 1, wherein R$^1$ is a C$_1$–C$_{20}$ alkyl, C$_3$–C$_7$-cycloalkyl, phenyl, naphthyl, or phenyl C$_1$–C$_6$ alkyl.

3. A composition according to claim 1, wherein R$^1$ represents a radical C$_n$H$_{2n+1}$ with n=1–12,
—(CH$_2$)$_m$— with m=2–12,

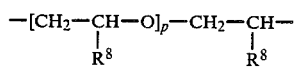

with
R$^8$=H or CH$_3$, and p=1–9,

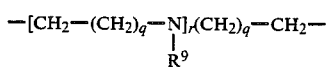

with
R$^9$=C$_1$–C$_4$-alkyl, q=1 or 2, and r=1–4,

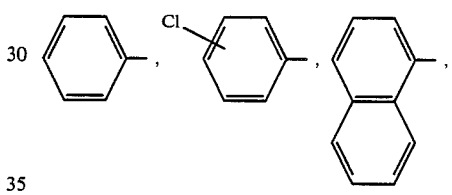

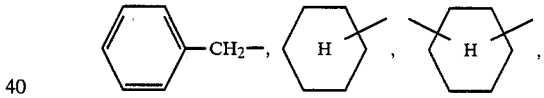

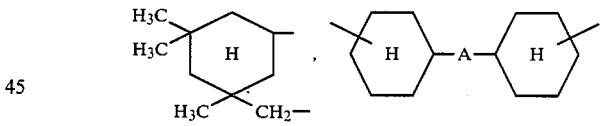

wherein
A=Alkylene having 1–4 carbon atoms,

—O— or —N—,
         |
        CH$_3$

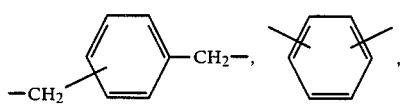

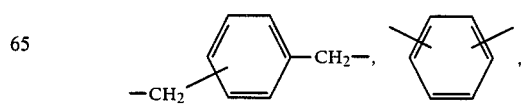

-continued

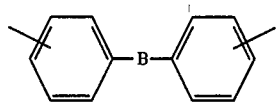

wherein
B=alkylene having 1-4 carbon atoms,

—O— or —N—,
           |
           CH₃

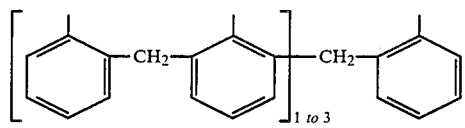

C₄H₉—O—CH₂CH₂CH₂—,

—(CH₂)₃—O—(CH₂)₂₋₃—O—(CH₂)₃—,

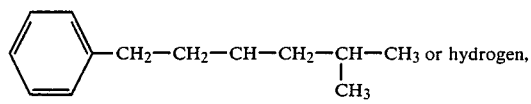—CH₂—CH₂—CH—CH₂—CH—CH₃ or hydrogen,
                                    |
                                    CH₃

$C_nH_{2n+1}$—C(=O)— with n = 1-3, or

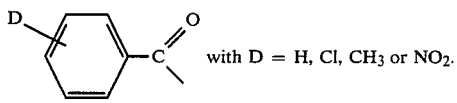 with D = H, Cl, CH₃ or NO₂.

4. A composition according to claim 1, wherein R² and R³ do not simultaneously represent acetyl when m=1.

5. A composition according to claim 1, wherein R¹ represents $C_nH_{2n+1}$— wherein n=1 to 12.

6. A composition according to claim 1, wherein R¹ represents —(CH₂)$_m$— wherein m=2 to 12.

7. A composition according to claim 1, wherein R¹ represents

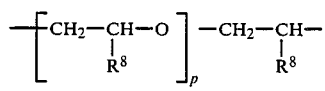

R⁸ = H, CH₃
p = 1–9.

8. A composition according to claim 1, wherein R¹ represents

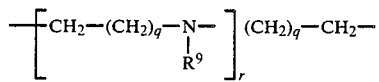

R⁹ = C₁—C₄—alkyl
q = 1–2
r = 1–4.

9. A composition according to claim 1, wherein R¹ represents

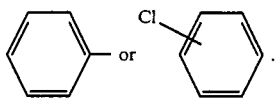

10. A composition according to claim 1, wherein R¹ represents

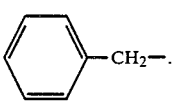

11. A composition according to claim 1, wherein R¹ represents

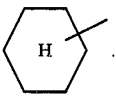

12. A composition according to claim 1, wherein R¹ represents

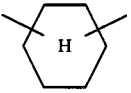

13. A composition according to claim 1, wherein R¹ represents

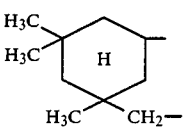

14. A composition according to claim 1, wherein R¹ represents

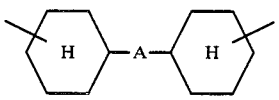

15. A composition according to claim 1, wherein R¹ represents

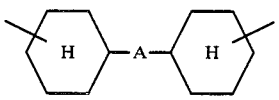

A = alkylene having 1-4 C atoms, O, —N(CH₃)—.

16. A composition according to claim 1, wherein R¹ represents

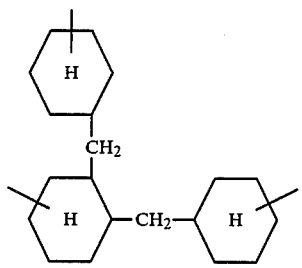

17. A composition according to claim 1, wherein $R^1$ represents

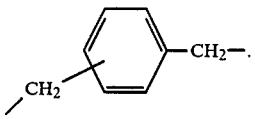

18. A composition according to claim 1, wherein $R^1$ represents

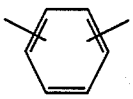

19. A composition according to claim 1, wherein $R^1$ represents

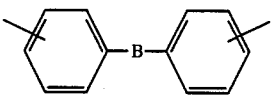

wherein
B=alkylene having 1-4 carbon atoms, O, or —N(CH₃)—.

20. A composition according to claim 1, wherein $R^1$ represents

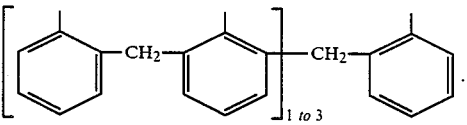

21. A composition according to claim 1, wherein $R^1$ represents

C₄H₉—O—CH₂—CH₂—CH₂—.

22. A composition according to claim 1, wherein $R^1$ represents

—(CH₂)₃—O—(CH₂)₂ to 4 O—(CH₂)₃—.

23. A composition according to claim 1, wherein $R^1$ represents

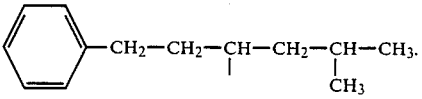

24. A composition according to claim 1, wherein $R^1$ represents

H—.

25. A composition according to claim 1, wherein $R^1$ represents

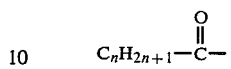

wherein
n=1 to 3.

26. A composition according to claim 1, wherein $R^1$ represents

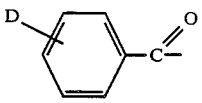

wherein
D=H, Cl, CH₃, or NO₂.

27. A composition according to claim 1, wherein $R^1$ is an acyl group and said acyl group is selected from the group consisting of acetyl, propionyl, n-butyryl, i-butyryl, benzoyl, toluoyl, xyloyl, m-chlorobenzoyl, m-nitrobenzoyl and p-nitrobenzoyl.

28. A composition according to claim 1, wherein m=1 or 2 and $R^2=R^3$=acetyl, propionyl or benzoyl, or m=1 and $R^1=R^2=R^3$acetyl, propionyl or benzoyl.

29. A composition according to claim 28, wherein said per-compound is an inorganic per compound.

30. A composition according to claim 29, wherein said per-compound is one which produces $H_2O_2$ in an aqueous solution.

31. A composition according to claim 30, wherein said inorganic per-compound is a perborate, persilicate, percarbonate or peroxyhydrate of an alkali metal.

32. A composition according to claim 29 wherein said inorganic per-compound is an orthophosphate, pyrophosphate, or polyphosphate of an alkali metal.

33. A bleaching composition comprising a bleach and the composition of claim 1.

34. A composition according to claim 33, wherein the composition of claim 1 is present in said bleaching composition in an amount of 10 to 100 percent by weight based upon the weight of the total composition.

35. A bleaching detergent composition comprising a bleaching detergent and the composition of claim 1.

36. A composition according to claim 35 wherein said bleaching detergent composition contains a composition of claim 1 in an amount of 5 to 50 percent by weight based upon the total weight of the composition.

37. A composition according to claim 1, wherein said activator is present in such composition such that there are 0.1 to 6 acyl radicals per active oxygen atom of the per compound.

38. A composition according to claim 1, wherein said activator is present in an amount such that there are 0.2 to 1 acyl radical per active oxygen atoms of the per-compound.

39. A bleaching agent or detergent comprising 5 to 50% by weight of a composition comprising per-compound and activator according to claim 1, 5–40 percent by weight of a surface-active agent, 10 to 80 percent by weight of a builder and 0 to 15 percent by weight of other auxiliaries and additives.

40. A composition comprising a per-compound and an activator, said activator being 1,2-ethane-diyl-4,4'-bis-[1,2-bis-acetyl-triazolidine-3,5-dione].

* * * * *